US006875452B1

(12) United States Patent
Fyfe

(10) Patent No.: US 6,875,452 B1
(45) Date of Patent: Apr. 5, 2005

(54) INHIBITOR AND PRESERVATIVE FORMULATION

(76) Inventor: Lorna Fyfe, 33 Joppa Road, Joppa, Edinburgh EH15 2HB (GB)

( * ) Notice: Subject to any disclaimer, the term of this patent is extended or adjusted under 35 U.S.C. 154(b) by 0 days.

(21) Appl. No.: 09/486,239

(22) PCT Filed: Aug. 21, 1998

(86) PCT No.: PCT/GB98/02425

§ 371 (c)(1),
(2), (4) Date: Feb. 23, 2000

(87) PCT Pub. No.: WO99/09836

PCT Pub. Date: Mar. 4, 1999

(30) Foreign Application Priority Data

Aug. 23, 1997 (GB) .............................................. 9717893
Sep. 4, 1997 (GB) .......................................... 9718691
Jan. 7, 1998 (GB) ............................................ 9800166

(51) Int. Cl.$^7$ ............................................. A61K 35/78
(52) U.S. Cl. ..................................................... 424/725
(58) Field of Search ............................. 424/725, 195.1, 424/49, 58

(56) References Cited

U.S. PATENT DOCUMENTS 4,945,087 A * 7/1990 Talwar et al. .................. 514/60
4,966,754 A * 10/1990 Purohit et al. ........... 424/195.1
5,443,817 A * 8/1995 Zimmerman et al. .......... 424/47
5,817,295 A * 10/1998 Chaudhari et al. ............. 424/49

OTHER PUBLICATIONS

Fyfe et al. Inhibition of *Listeria monocytogenes* and *Salmonella enteriditis* by Combinations of Plant Oils and Derivatives of Benzoic Acid: The Development of Synergistic Antimicrobial Combinations; Int. Journal of Antimicrobial Agents 9 (1998) pp. 195–199.*

Fyfe, L., et al. (abstract). (1997). Inhibition of *Listeria monocytogenes* and *Salmonella enteriditis* by Combinations of Plant Oils and Derivatives of Benzoic Acid: The Development of synergistic Antimicrobial Combinations. *Int J Antimicrob Agents.* 9(3): 195–199.

Hodgson, I., et al. (abstract). (1998). Inhibition of Bacteria and Yeast by Oil of Fennel and Paraban: Development of Synergistic Antimicrobial Combinations. *Journal of Essential Oil Research.* 78:1216–1220.

Lachowicz, K.J., et al. (abstract). (1998). The Synergistic Preservative Effects of the Essential Oils of Sweet Basil (ocimum basilicum L.) Against Acid–Tolerant Food Microflora. *Letters in Applied Microbiology.* 26(3):209–214.

Wan, J., et al. (abstract). (1998). The Effect of Essential Oils of Basil on the Growth of Aeromonas Hydrophilia and Pseudomonas Fluorescens. *Journal of Applied Microbiology.* 84(2):152–158.

El–Gengaihi, S., et al. (abstract). (1982). Biological Investigation of Some Essential Oils Isolated from Egyptian Plants. *Pharm. Sci. Lab. Natl. Res. Cent.* 21(1):107–111.

Sinha, G.K., et al. (abstract). (1990). Antibacterial and Antifungal Study of Some Essential Oils and Some of their Constitutents. *Indian Perfum.* 34(2):126–129.

Arora, R., et al. (abstract). (1984). Application of Essential Oils and Their Isolates as Preservative of Citrus–Reticulata. *Biol. Mem.* 9(1):98–104.

* cited by examiner

*Primary Examiner*—Patricia Leith
(74) *Attorney, Agent, or Firm*—Teresa O. Bittenbender; Dechert, LLP; Joseph R. Heffern

(57) ABSTRACT

The present invention provides an inhibitor and preservative formulation comprising a combination of a plant oil chosen from the oils of fennel, anise or basic, or derivatives or active ingredients thereof with benzoic acid, methyl paraben, ethyl paraben, propyl paraben or butyl paraben. Suitably the formulation comprises between 0.1% and 1% of plant oil derivative or active ingredient thereof and 0.1% benzoic acid or paraben. The ingredients may be administered separately or together to a foodstuff. Alternatively the ingredients may be used in the manufacture of medicament to inhibit micro-organism growth.

16 Claims, No Drawings

INHIBITOR AND PRESERVATIVE FORMULATION

This application claims the benefit of priority of GB 9717893.3; filed on Aug. 23, 1997, of GB 9718691.0, filed on Sep. 4, 1997, of GB 9800166.2, filed on Jan. 7, 1998, and of WO 99/09836, filed on Aug. 21, 1998, the contents of each are incorporated by reference in their entireties.

The present invention relates to food preservatives and medical inhibitors. In particular the invention relates to formulations which can inhibit *Listeria monocytogenes; Salmonella enteriditis; Staphylococcus aureus* and vancomycin-resistant *Enterococcus*.

*Listeria monocytogenes* and *Salmonella enteriditis* are food-borne pathogens responsible for the significant increase in food-borne diseases observed over the past few years [1]. Susceptible individuals tend to be the very young, old and pregnant women who are particularly susceptible to listeriosis [2]. There are a variety of "traditional" procedures used to control these micro-organisms including good hygiene procedures, pressure and heat [3] however there is little evidence of the widespread use of an effective synergistic combination preservative system to limit the control of infection. Individual preservatives have been used over the years such as organic acids [4] and nisin [5] which has been used to inhibit *L. monocytogenes*. This micro-organism unlike *S. enteriditis* is capable of growth at 4° C. and can readily achieve an infectious dose even at this low refrigeration temperature [6].

This invention also relates to inhibition of a bacteria such as multi (methicillin) resistant *Staphylococcus aureus* and vancomycin-resistant *Enterococcus*. As the names of these micro-organisms imply they are resistant to anitbiotics and there is consequently a great need to develop a preservative system which will not only inhibit the bacterium but reduce the possibility of the generation of resistant strains.

Elimination of these organisms has centred on the use of antibiotics. However, microorganisms can become resistant to antibiotics.

Inhibitory properties of plant oils have been known for some years [7] and recently Tassov et al, [8] described inhibition of *S. enteriditis* and *L. monocytogenes* in a model food system at 4° C. and 10° C. by oil of mint.

Benzoic acid has been found as a "natural" breakdown product in several milk-based products such as yoghurt, milk and cheese and is one of the first and most widely used preservatives in the world because it is relatively inexpensive and has low toxicity [9]. Furthermore, it has been shown to be inhibitory against food poisoning and spore forming bacteria [9] and has been shown to act synergistically with several components against a variety of micro-organisms [10].

Phenolic compounds such as methyl paraben (esters of p-hydroxybenzoic acid) have been licensed for direct use in foods at a concentration not exceeding 0.1% [11].

It is an object of the present invention to provide a formulation suitable for use in food and in hospital environments which will effectively inhibit growth of microorganisms.

According to one aspect of the present invention there is provided a formulation for use as an inhibitor or a preservative comprising a combination of plant oil chosen from oils of fennel, anise or basil, or derivatives or active ingredients thereof with benzoic acid, methyl paraben, ethyl paraben, propyl paraben or butyl paraben.

The plant oil derivatives or active ingredients include trans-anethole, fenchone and estragole.

The plant oil or derivative or active ingredient thereof and the benzoic acid or paraben may be administered separately or together to a foodstuff.

The plant oil or derivative or active ingredient thereof and the benzoic acid or paraben may be adminstered in the form of a spray. Suitably the formulation can be administered to surfaces as inhibitor to prevent micro-organism growth.

Typically the preservative combination is prepared as a concentrated solution for addition to foodstuffs or could be used to decontaminate inanimate objects such as work benches or utensils.

Preferably the preservative is used such that the concentration of plant oil, derivative or active ingredient thereof is between 0.01% to 1% and the concentration of benzoic acid or paraben is from 0.01% to 1%.

In one embodiment the invention comprises oil of fennel and methyl paraben wherein the oil of fennel is used at a concentration of 0.2% and the methyl paraben is used at a concentration of 0.1%.

In another aspect the invention provides a preservative comprising oil of basil.

Preferably the oil of basil is used at a concentration of 0.01% to 0.5%.

The invention further provides use of oil of basil as an inhibitor of *L. monocytogenes, S. enteriditis, S. aureus* and vancomycin-resistant *Enterococcus*.

In a second embodiment the invention comprises fenchone and methyl paraben wherein the fenchone is used at a concentration of 0.1% and the methyl paraben is used at a concentration of 0.1%.

In another aspect the invention provides a preservative comprising trans-anethole.

In yet another aspect the invention provides a preservative comprising estragole (4-aliylanisole).

The invention further provides use of trans-anethole and estragole as inhibitors of *L. monocytogenes, S. enteriditis, S. aureus* and vancomycin-resistant *Enterococcus*.

The invention further provides use of an active ingredient chosen from oils of fennel, anise or basil, chosen from fenchone, trans-anethole or estragole in combination with methyl paraben in the preparation of a composition for the inhibition of *L. monocytogenes* or *S. enteriditis, S. aureus* or vancomycin-resistant *Enterococcus*.

The invention further provides use of a plant oil chosen from oil of fennel, oil of basil or oil of anise in combination with methyl paraben or benzoic acid in the preparation of a composition for the inhibition of *L. monocytogenes, S. enteriditis, S. aureus* or vancomycin-resistant *Enterococcus*.

Several combinations according to the invention exhibit synergistic antimicrobial properties which enable one or more component of the combination to be used at a relatively low concentration. This is clearly useful in terms of cost, but more importantly could be more acceptable to the general public who have become increasingly critical of the use of chemical preservatives in food. In addition a combination containing a plant oil may be perceived as natural rather than chemical.

The present invention also provides a composition for use in inhibiting pathogen infection, said composition comprising at least one oil chosen from oil of fennel and oil of anise or the active ingredients thereof together with at least one member of the group consisting of benzoic acid, methyl, ethyl, propyl and butyl paraben.

Typically a composition may comprise the active ingredients in amounts as follows:

| | |
|---|---|
| Oil of Fennel | Preferably 0–1%, more preferably 0.1–0.4% and most preferably 0.15–0.25% |
| Oil of Anise | Preferably 0–1%, more preferably 0.1–0.4% and most preferably 0.15–0.25% |
| Benzoic Acid | Preferably 0–1%, more preferably 0.05–0.5% and most preferably 0.05–0.15% |
| Methyl Paraben | Preferably 0–1%, more preferably 0.05–0.5% and most preferably 0.05–0.15% |
| Ethyl Paraben | Preferably 0–1%, more preferably 0.05–0.5% and most preferably 0.05–0.15% |
| Propyl Paraben | Preferably 0–1%, more preferably 0.05–0.5% and most preferably 0.05–0.15% |
| Butyl Paraben | Preferably 0–1%, more preferably 0.05–0.5% and most preferably 0.05–0.15% |

The term "composition" is used herein to include separate formulations which are intended for co-administration, either sequentially or simultaneously. It is generally more convenient however for the composition to be a single mixture formulation.

A preferred embodiment of the invention provides a composition for use in inhibiting Staphylococcus aureus or vancomycin-resistant Enterococcus, the composition comprising 0.15–0.25% of at least one of oil of fennel and oil of anise in combination with 0.05–0.15% of at least one of the group consisting of benzoic acid, methyl, ethyl, propyl and butyl paraben.

The composition according to the invention may be administered in any convenient form. Mention may be made of tablets, solutions, suspensions and also aerosol sprays. The composition may be administered enterally, palentrally, subcutaneously, (via a subcutaneous patch or injections), intra muscularly and so on.

In another aspect, the present invention provides the use of a composition as described herein in the manufacture of a medicament to inhibit *Staphylococcus aureus* and vanconcycin-resistant *Enterococcus*.

In a further aspect, the present invention provides a method of inhibiting *Staphylococcus aureus* and vancomycin-resistant *Enterococcus*, in human or non-human (preferably mammalian) animal body, said method comprising administering to said body a composition as described above.

The active ingredients of the composition may be in combination with any pharmaceutically acceptable carrier.

One preferred carrier is water.

A particularity preferred form of application is as a sprayable formulation.

The invention is illustrated with reference to the following examples and results are summarised in the accompanying tables.

EXAMPLES

Materials and Methods
Maintenance of Bacteria

*Listeria monocytogenes* 11994 and *Salmonella enteriditis* 4444 were purchased from the National Collection Type Culture, Porton Down, Wiltshire, UK. Each was stored in the long term in glycerol at −20° C., in the medium term on Tryptone Soya Agar (TSA) slopes and in the short term on TSA plates. All agar and broth (Tryptone Soya Broth) was purchased from Oxoid-Unipath Limited, Basingstoke, UK.
Reagents Oils of fennel, anise and basil were generously supplied by F D Copeland and Sons Limited, Colanol House, 5 Westfield Street, London, UK. Trans-anethole, fenchone, estragole (4-allylanisole), benzoic acid, methyl paraben and phosphate buffered saline (PBS) were purchased from Sigma-Aldrich Company Limited, Poole, Dorset, UK.
Experimental Procedure (1)

10 $\mu$l of an overnight TSB culture of *L. monocytogenes* or *S. enteriditis* incubated at 37° C. was added to 10 ml of TSB containing 0.2% of oil of fennel, 0.2% oil of anise, 0.2% or 0.02% oil of basil in combination with 0.1% benzoic acid or 0.1% methyl paraben. Corresponding controls were also prepared thus 10 $\mu$l of each overnight culture was added to the appropriate broth only. All tubes were incubated at 37° C. 1 ml samples were removed from each test and control after vortexing at 0 hrs, 1 hr, 4 hrs, 8 hrs, 24 hrs and 48 hrs and serially diluted in 0.01M PBS. 100 $\mu$l from each dilution was placed on an agar plate and spread across the surface. Plates were incubated at 37° C. and colonies counted as colony forming units per ml (cfu/ml). As ethanol was used to prepare solutions of benzoic acid and methyl paraben a diluent control was used where ethanol was added to each culture medium. The ethanol present was shown not to exhibit any inhibitory properties against micro-organisms tested. Due to the limitation of the serial dilution technique it was not possible to count cfu less than 10/ml.

Oils of fennel and anise were used at 0.2% and whilst oil of basil was originally used for comparative purposes at 0.2% it was later used at 0.02%. Benzoic acid and methyl paraben were used at 0.1%. Several factors were considered when choosing these concentrations. Firstly, to determine the presence of synergistic inhibition by a combination it was necessary to use each component of the combination at a concentration which was relatively weakly inhibitory over the timescale of the experiment. Secondly, with respect to benzoic acid and methyl paraben these cannot be used in foods in excess of 0.1% [11].
Reproducibility Triplicate plates were prepared for each dilution and the mean count of three plates was determined. The standard error of the mean was $\leq 10\%$. Each experiment was performed on three separate occasions. It is the mean count from three separate experiments and the corresponding standard error of the mean which are shown in the results section.
Statistical Test Two-tailed paired student's t-test was used to analyse inhibition caused by a combination compared to the corresponding control. Differences were judged to be statistically significant when $p<0.05$.
Definition of Synergy The definition used is that of Eliopoulos and Moellering [12] thus inhibition is defined as synergistic when the combined preservatives demonstrate $\geq 1$ $\log_{10}$ greater inhibition than the sum of the inhibitory effects of the preservatives used alone. This definition is also in agreement with Mims et al [13].
Results
*Listeria monocytogenes*

Oil of basil at 0.2% was a potent inhibitor of this micro-organism where at 4 hrs, 8 hrs, 24 hrs and 48 hrs there was $<1.0$ $\log_{10}$ cfu/ml (Table 1A). Even at only 1 hr of culture there was a count of only 3.4 $\log_{10}$ cfu/ml which represents a reduction of 3.0 $\log_{10}$ compared to the corresponding control. Oil of fennel at 0.2% was less inhibitory although there were reductions of 3.0 $\log_{10}$, 2.9 logo and 0.6 $\log_{10}$ at 8 hrs, 24 hrs and 48 hrs compared to corresponding controls. Oil of anise was relatively weakly inhibitory over the 48 hr period, as were benzoic acid and methyl paraben.

For all combinations those containing methyl paraben were more inhibitory than those containing benzoic acid.

For oil of anise in combination with benzoic acid there were reductions of 1.3 $\log_{10}$, 2.6 $\log_{10}$, 2.1 $\log_{10}$ and 0.5 $\log_{10}$ at 4 hrs, 8 hrs, 24 hrs and 48 hrs compared to corresponding controls. Greater inhibition of growth was however observed with the combination of oil of anise and methyl paraben. Thus at the same times as above there were reductions of 1.7 $\log_{10}$, 3.4 $\log_{10}$, 5.1 $\log_{10}$ and 6.6 $\log_{10}$ respectively.

Combinations containing oil of fennel were more inhibitory than those containing oil of anise. Thus compared to corresponding controls, there were reductions of 1.9 $\log_{10}$, 3.6 $\log_{10}$, 4.2 $\log_{10}$ and 4.2 $\log_{10}$ for oil of fennel and benzoic acid; and reductions of 2.1 $\log_{10}$, 4.5 $\log_{10}$, 5.7 $\log_{10}$ and 7.1 $\log_{10}$ for combinations of oil of fennel and methyl paraben at 4 hrs, 8 hrs, 24 hrs and 48 hrs respectively.

With respect to synergistic inhibition this was evident after 24 hrs and 48 hrs of culture for combinations of oil of anise with methyl paraben and combinations of oil of fennel with benzoic acid or methyl paraben at the same times. In the first example there was 4.6 $\log_{10}$ and 6.5 $\log_{10}$ further inhibition of growth by the combination compared to the additive inhibition by each separate component. For oil of fennel with benzoic acid there was 1 $\log_{10}$ and 3.7 $\log_{10}$ further inhibition of growth by the combination and for oil of fennel with methyl paraben there was 2.8 $\log_{10}$ and 6.7 $\log_{10}$ further inhibition by each combination compared to additive inhibition by separate preservatives also at 24 hrs and 48 hrs.

As mentioned previously 0.2% oil of basil was a potent inhibitor of *L. monocytogenes* in its own right and it was consequently difficult to determine synergistic inhibition of a combination containing basil at this concentration. Indeed this may explain why combinations containing 0.2% oil of basil with either benzoic acid or methyl paraben were no more inhibitory than the oil on its own. 0.02% oil of basil on the other hand was more or less bacteriostatic over the 48 hr period with a reduction in growth of 1.3 $\log_{10}$, 2.5 logo 3.3 $\log_{10}$ and 1.5 $\log_{10}$ at 4 hrs, 8 hrs, 24 hrs and 48 hrs.

The combination of 0.02% oil of basil and benzoic acid was no more inhibitory than the oil on its own at 0.02%. The same was also true for oil of basil in combination with methyl paraben at 1 hr and 4 hrs but not 24 hrs and 48 hrs where there was inhibition of growth by 5.0 $\log_{10}$ and 6.4 $\log_{10}$ respectively. Furthermore, synergistic inhibition was evident at these times where there was a further reduction of 1.7 $\log_{10}$ and 5.1 $\log_{10}$ by the combination compared to the additive inhibition by each separate preservative.

Salmonella enteriditis

Individual oils at 0.2% and combinations of oils with benzoic acid or methyl paraben were generally more inhibitory against *Salmonella* enteriditis than *Listeria monocytogenes* (Table 1B). Oil of basil at 0.2% was the most potent oil thus there was <1.0 $\log_{10}$ cfu/ml at all times of culture except 1 hr where there was a count of only 1.4 $\log_{10}$ which in fact represented a reduction of 4.6 $\log_{10}$ compared to the corresponding control. Oils of anise and fennel exhibited a similar pattern of inhibition up to 48 hrs at which time there was inhibition of growth of only 2.6 $\log_{10}$ by oil of anise and 4.0 $\log_{10}$ by oil of fennel.

Benzoic acid and methyl paraben exhibited little inhibition over the 48 hr period.

As with *Listeria monocytogenes* a combination of preservatives containing methyl paraben was more inhibitory than one containing benzoic acid. Thus for oil of anise or fennel in combination with methyl paraben there was <1.0 $\log_{10}$ cfu/ml at all times of culture; which represents approximately a >5.0 $\log_{10}$ reduction in number at all times compared to corresponding controls. In contrast there was, in general, a reduction of only 1 to 3 $\log_{10}$ cfu/ml at all times for combinations of oil of anise or fennel with benzoic acid.

Synergistic inhibition was evident for combinations of oil of anise or oil of fennel with methyl paraben at all times of culture. In the case of the former there was a further reduction in number of >2.6 $\log_{10}$, >2.2 $\log_{10}$, >2.4 $\log_{10}$, >6.3 $\log_{10}$ and >4.8 $\log_{10}$ cfu/ml at 1 hr, 4 hrs, 8 hrs, 24 hrs and 48 hrs respectively compared to the additive inhibition by each separate preservative. In the latter, there was a further reduction of >3.3 logo, >2.7 $\log_1$, >3.0 $\log_{10}$, >6.6 $\log_{10}$ and 3.3 $\log_{10}$ by the combination compared to the additive inhibition by the separate components.

The combination of oil of basil (0.2%) and benzoic acid was less inhibitory than oil of basil (0.2%) on its own. In contrast the combination of oil of basil (0.2%) and methyl paraben was as inhibitory as the individual oil where there was <0.1 $\log_{10}$ cfu/ml at all times of culture. Oil of basil at 0.02% was weakly inhibitory against *S. enteriditis* and even in combination with benzoic acid or methyl paraben there was little inhibition of growth.

Discussion

It has been recognised for some time that no single preservative will be completely effective against microorganisms which contaminate food. Combination preservatives such as those described here, therefore seem preferable as they will have the potential to eliminate a broad range of microbes and will be more effective than single preservatives because of their multiple modes of action. Furthermore as plant oils contain many active ingredients it would be unlikely that micro-organisms would be able to mutate a sufficient number of genes to generate resistant strains for survival.

Synergistic effects by combinations of preservatives have been well documented. However, this is the first reported case of synergistic inhibition by combinations of plant oils and derivatives of paraben against two of the major causes of food-borne illness namely *L. monocytogenes* and *S. enteriditis*. Oils used were fennel, anise and basil as they have similar active ingredients [14]. Peliminary studies suggest that these combinations would be effective against other micro-organisms including *S. aureus* and vancomycin-resistant *Enterocyccus*.

In this study combinations containing oil of fennel were more inhibitory than those containing comparable concentrations of oil of anise or basil. Although all have estragole in common, oils of fennel and anise contain anethole but the increased activity of combinations containing fennel may be due to active ingredients which are unique to fennel such as fenchone and alpha pinene [14].

Combinations containing methyl paraben were more inhibitory than those containing benzoic acid.

Phenolic compounds such as methyl paraben are known to be more inhibitory than benzoic acid [15], however a drawback with this paraben is its increased toxicity and taste. These may not however be disadvantageous within a combination which is synergistic (as most of the methyl paraben containing combinations have been described in this study) as one or indeed both compounds of the combination could be used at a relatively low concentration.

It is clear from this study that *S. enteriditis* was more susceptible to inhibition by each combination than *L. monocytogenes*. It is unclear at this stage why this should be, but the obvious difference between these two micro-organisms is the structure of the cell wall and it may be that this is one or more of the targets of each combination. In this regard paraben and benzoic acid have been shown to disrupt bacterial cell walls [16] and it is reasonable to suggest that damage to the cell wall could then facilitate the uptake of oil so that it then reaches its intracellular target. This mechanism of synergy is in agreement with the permeabilization synergy of Denyer et al [17]. The precise mode of action of each combination will be the subject of future investigations.

Much emphasis has been placed on the activity of each combination but it is important to point out the potent activity of oil of basil on its own, where for both microorganisms there was less than 10 cfu/ml after only 4 hours of culture in 0.2% of basil. It would be interesting to further determine the properties of this oil in both broth and food.

Although this study investigated the activity of combinations of plant oils and chemical preservatives over a 48 hour period, at one pH (physiological pH) and only in laboratory medium, it does show the potential of these novel combinations as potent inhibitors of *L. monocytogenes* but in particular *S. enteriditis*. Further studies will consider each of the above points however emphasis will be placed on inhibitory experiments at lower temperatures such as 4° C. and 10° C. Indeed it has previously been mentioned that *L. monocytogenes* can grow at 4° C. More recently Jones et al, 1997 [18] have shown the fatty acid composition of the cell wall of this microbe to change at 4° C. It would be interesting to discover if these cells could be further inhibited by a combination at lower temperatures.

Experimental Procedure (2)

10 μg of an overnight culture of *L. monocytogenes* or *S. enteriditis* incubated at 37° C. was added to 10 ml of TSB containing 0.1% of trans-anethole, fenchone or estragole in combination with 0.1% methyl paraben. Corresponding controls were also prepared, thus 10 μl of each overnight culture was added to the appropriate broth only. All tubes were incubated at 37° C. 1 ml samples were removed from each test and control after vortexing at 0 hrs, 1 hr, 4 hrs, 8 hrs, 24 hrs and 48 hrs and serially diluted in 0.01M PBS. 100 μl from each dilution was placed on an agar plate and spread across the surface. Plates were incubated at 37° C. and colonies counted as colony forming units per ml (cfu/ml). As ethanol was used to prepare stock solutions of methyl paraben a diluent control was used where ethanol was added to each culture medium. The ethanol present was shown not to exhibit any inhibitory properties against the microbes tested. Due to the limitation of the serial dilution technique it was not possible to count cfu less than 10/ml.

To determine the presence of synergy within a combination it was necessary to use a concentration of trans-anethole, fenchone, estragole and methyl paraben which was relatively weakly inhibitory in its own right over the timescale of the experiment. Furthermore to make valid comparison about the activity of each combination against each microbe it was necessary to use just one concentration of each component with the combination. Preliminary data from the laboratory indicated that 0.1% would fulfil each of the criteria above. In addition, methyl paraben cannot be used in food in excess of 0.1% [15].

Reproducibility
As in Experimental Procedure (1)
Statistical Test
As in Experimental Procedure (1)
Definition of Synergy
As in Experimental Procedure (1)
Results
*Listeria monocytogenes*

From Table 2A it can be seen that fenchone was the most inhibitory single component against this micro-organism. At times of 8 hrs and above, cells were undetectable (<10 cfu/ml), even at 1 hr and 4 hrs there was a reduction of 4 to 5 $\log_{10}$ cfu/ml compared to the control. For estragole there was more than 4 $\log_{10}$ inhibition of growth after 24 hrs. In contrast methyl paraben and trans-anethole had little or no inhibitory properties against *L. monocytogenes*.

The most inhibitory combination was fenchone and methyl paraben. Here the pattern of inhibition was almost identical to that observed for fenchone alone. Synergistic inhibition was not however detectable.

For estragole and methyl paraben there was more than 4.0 $\log_{10}$ inhibition of growth at 8 hrs or above. This inhibition was also synergistic being 2.0 $\log_{10}$ more than the additive inhibition of the separate preservatives. With trans-anethole and methyl paraben growth was reduced by 4.0 $\log_{10}$ or more at 24 hrs and 48 hrs. This reduction was synergistic being 4.0 $\log_{10}$ more than with separate preservatives.

*Salmonella enteriditis*

From Table 2B it can be seen that estragole and trans-antheole were the two most single inhibitory preservatives against *S. enteriditis*. Here growth was inhibited at 4 hrs and 8 hrs by more than 5.0 $\log_{10}$ for estragole and over 2.0 $\log_{10}$ for trans-anethole. Interestingly, numbers seemed to recover at 48 hrs where inhibition was 2.1 log and 1.0 $\log_{10}$ for estragole and trans-anethole respectively. Methyl paraben and fenchone exhibited little or no inhibition over the 48 hr period.

Combinations of estragole or trans-anethole and methyl paraben were potent inhibitors of S. enteriditis where after 4 hrs cells were undetectable (<10 cfu/ml). Even after 1 hr, growth was reduced by both combinations by almost 5 $\log_{10}$.

Synergistic inhibition was evident at 24 hrs and 48 hrs for estragole and methyl paraben where there was over 2 $\log_{10}$ and 5 $\log_{10}$ more inhibition than with separate preservatives. For trans-anethole and methyl paraben inhibition was synergistic at all times where there was over 2.5 $\log_{10}$ inhibition than with separate components up to and including 8 hrs. At 24 hrs and 48 hrs there was more than 6.0 $\log_{10}$ further inhibition by the combination compared to inhibition by separate agents.

Fenchone and methyl paraben was the least inhibitory combination against *S. enteriditis*, however growth was inhibited by over 2.0 $\log_{10}$ at 4 hrs and 8 hrs and almost 5 $\log_{10}$ at 24 hrs and 48 hrs. Synergistic inhibition was detected at all times of culture but was particularly noticeable at 24 hrs and 48 hrs where there was almost 4.0 $\log_{10}$ more inhibition by the combination compared to additive inhibition by separate components.

Discussion

There are several advantages a combination preservative system has over a single preservative. These are the potential to inhibit a greater number and range of micro-organisms, the possibility of reducing the generation of resistant strains and the development of synergistic inhibition. In the last example one or more components could be used at a relatively low concentration which would be desirable in terms of reduced cost and toxicity.

Although paraben is a chemical preservative, the fact that the other component in each combination was a plant oil, often perceived as a natural product, may be acceptable to the general public who have become increasingly critical of the use of chemical preservatives in food.

Plant oils however contain many active ingredients and are often reported to be harmful in high doses [19]. In this study three plant oil components common to oils of fennel, anise or basil were investigated. All three are plant terpenoids [19] with fenchone being a terpenoid ketone and estragole a terpenoid ether. Fenchone and trans-anethole are described as non-toxic, indeed the latter is used in food flavourings [20,21]. Estragole is probably the most harmful component being carcinogenic in high doses in mice, however low doses are thought to be detoxified in humans [22,23].

Fortunately in this study relatively low doses of each terpenoid (0.1%) were shown to synergistically inhibit *L. monocytogenes* or *S. enteriditis* when in combination with 0.1% methyl paraben. There were however clear differences in the sensitivities of each micro-organism to inhibition by combinations of terpenoids and methyl paraben and also to individual terpenoids.

*L. monocytogenes* even at early stages of culture was particularly sensitive to inhibition by fenchone on its own and fenchone in combination with methyl paraben. So potent was this activity of fenchone that it was not possible to detect synergistic inhibition by the combination. The other combinations although less inhibitory were still effective synergistic inhibitors of growth particularly at the later stages of culture. In contrast, *S. enteriditis* was less sensitive to inhibition by fenchone whether on its own or in combination with methyl paraben although significant synergistic inhibition was detected at all times of culture. Potent inhibition, even at early stages of culture, was observed with combinations of trans-anethole or estragole and methyl paraben. These differences in sensitivities to inhibition of *L. monocytogenes* and *S. enteriditis* by each combination of terpenoid and methyl paraben may shed light on their respective mode(s) of action which may be associated with the structure of the microbial cell membrane of a Gram-positive and Gram-negative bacterium. Paraben is known to disrupt the microbial cell membrane [15] and it is reasonable to suggest that this disruption may enhance the activity of the terpenoid or facilitate its entrance into the cell.

Although this study was conducted in laboratory medium at 37° C. further studies will determine the potential of these novel combinations of terpenoid and paraben as inhibitors of food-borne pathogens.

Combinations tested herein have been shown in preliminary studies to be effective against *S. aureus* and vancomycin-resistant *Enterococcus*.

Formulations of the invention can be used as preservatives in food, as active ingredients in medicaments, in spray formulations to decontaminate surfaces and utensils. Regardless of the use of the formulation the mode of action will prevent growth of micro-organisms such as *Listeria monocytogenes, Salmonella enteriditis, Staphylococcus aureus* and vancomycin resistant *Enterococcus*.

| | | | | | |
|---|---|---|---|---|---|
| Control | 5.9 ± 0.04 | 6.8 ± 0.07 | 7.5 ± 0.1 | 9.0 ± 0.01 | 9.0 ± 0.04 |
| Estragole | 2.2 ± 0.05Δ | 1.6 ± 0.08Δ | 1.5 ± 0.08Δ | 4.3 ± 0.03Δ | 6.9 ± 0.03Δ |
| Trans-anethole | 4.9 ± 0.05Δ | 4.2 ± 0.04Δ | 4.5 ± 0.04Δ | 7.9 ± 0.04Δ | 7.9 ± 0.04Δ |
| Fenchone | 5.8 ± 0.02 | 6.4 ± 0.04 | 6.9 ± 0.04Δ | 8.6 ± 0.09Δ | 8.5 ± 0.01Δ |
| Methyl paraben | 6.0 ± 0.01 | 6.3 ± 0.01 | 6.6 ± 0.06Δ | 8.5 ± 0.04Δ | 8.6 ± 0.01Δ |
| Estragole and methyl paraben | 1.2 ± 0.06Δ | <1.0Δ | <1.0Δ | <1.0Δ* | <1.0Δ* |
| Trans-anethole & methyl paraben | 1.1 ± 0.04Δ* | <1.0Δ* | <1.0Δ* | <1.0Δ* | <1.0Δ* |
| Fenchone and methyl paraben expected | 4.7 ± 0.05Δ* | 4.3 ± 0.09Δ* | 4.3 ± 0.16Δ* | 4.1 ± 0.08Δ* | 4.2 ± 0.01Δ* |

All preservatives were used at a final concentration of 0.1%.
*= synergistic inhibition
Δ = p (0.05 inhibition compared to that of corresponding control. Numbers represent $\log_{10}$ of the mean count ± 1 SEM from three separate experiments.

TABLE 1

Inhibition of *Listeria monocytogenes* and *Salmonella enteriditis* by combinations of plant oils and benzoic acid or methyl paraben at 37° C. over a period of 48 hours.

| Time | 0 hrs | 1 hr | 4 hrs | 8 hrs | 24 hrs | 48 hrs |
|---|---|---|---|---|---|---|
| | | | 1A *Listeria monocytogenes* | | | |
| Control | 6.45 ± 0.02 | 6.46 ± 0.02 | 7.43 ± 0.04 | 8.63 ± 0.09 | 9.3 ± 0.03 | 9.06 ± 0.04 |
| OA | 6.45 ± 0.02 | 6.13 ± 0.01 | 6.27 ± 0.04 | 6.64 ± 0.16 | 8.76 ± 0.01 | 8.96 ± 0.03 |
| OF | 6.45 ± 0.02 | 5.9 ± 0.12 | 5.74 ± 0.11 | 5.67 ± 0.29Δ | 6.42 ± 0.41Δ | 8.53 ± 0.33Δ |
| OB | 6.45 ± 0.02 | 3.42 ± 0.3Δ | <1.0Δ | <1.0Δ | <1.0Δ | <1.0Δ |
| BA | 6.45 ± 0.02 | 6.33 ± 0.11 | 7.22 ± 0.04 | 8.16 ± 0.06 | 9.09 ± 0.03 | 9.0 ± 0.06 |
| MP | 6.45 ± 0.02 | 6.49 ± 0.01 | 7.02 ± 0.02 | 7.86 ± 0.05 | 9.27 ± 0.02 | 9.24 ± 0.02 |
| OA/BA | 6.45 ± 0.02 | 6.23 ± 0.04 | 6.09 ± 01Δ | 6.04 ± 0.16Δ | 7.21 ± 0.36Δ | 8.58 ± 0.13Δ |
| OA/MP | 6.45 ± 0.02 | 5.93 ± 0.05 | 5.71 ± 0.03Δ | 5.27 ± 0.17Δ | 4.16 ± 0.37*Δ | 2.5 ± 0.16*Δ |
| OF/BA | 6.45 ± 0.02 | 5.96 ± 0.05 | 5.55 ± 0.10Δ | 5.06 ± 0.42Δ | 5.07 ± 0.27*Δ | 4.77 ± 0.36*Δ |
| OF/MP | 6.45 ± 0.02 | 5.57 ± 0.22 | 5.3 ± 0.12Δ | 4.18 ± 0.29Δ | 3.64 ± 0.18*Δ | 1.99 ± 0.09*Δ |
| OB/BA | 6.45 ± 0.02 | 2.77 ± 0.11Δ | <1.0Δ | <1.0Δ | <1.0Δ | <1.0Δ |
| OB/MP | 6.45 ± 0.02 | 3.1 ± 0.08Δ | <1.0Δ | <1.0Δ | <1.0Δ | <1.0Δ |
| OB' | 6.45 ± 0.02 | 6.15 ± 0.07 | 6.18 ± 0.16Δ | 6.11 ± 0.24Δ | 6.04 ± 0.18Δ | 7.53 ± 0.22Δ |
| OB'/BA | 6.45 ± 0.02 | 6.10 ± 0.03 | 5.91 ± 0.09Δ | 5.93 ± 0.09Δ | 5.97 ± 0.57Δ | 7.46 ± 0.20Δ |
| OB'/MP | 6.45 ± 0.02 | 6.09 ± 0.08 | 5.92 ± 0.06Δ | 5.66 ± 0.88Δ | 4.33 ± 0.18*Δ | 2.64 ± 0.18*Δ |
| | | | 1B *Salmonella enteriditis* | | | |
| Control | 6.08 ± 0.03 | 6.05 ± 0.02 | 6.81 ± 0.02 | 8.20 ± 0.06 | 9.04 ± 0.05 | 9.10 ± 0.04 |
| OA | 6.08 ± 0.03 | 3.60 ± 0.21Δ | 3.75 ± 0.28Δ | 5.03 ± 0.36Δ | 8.04 ± 0.1Δ | 6.50 ± 0.50Δ |

TABLE 1-continued

Inhibition of *Listeria monocytogenes* and *Salmonella enteriditis* by combinations of plant oils and benzoic acid or methyl paraben at 37° C. over a period of 48 hours.

| Time | 0 hrs | 1 hr | 4 hrs | 8 hrs | 24 hrs | 48 hrs |
|---|---|---|---|---|---|---|
| OF | 6.08 ± 0.03 | 4.22 ± 0.07Δ | 4.20 ± 0.26Δ | 5.65 ± 0.32Δ | 8.36 ± 0.03Δ | 5.13 ± 0.11Δ |
| OB | 6.08 ± 0.03 | 1.43 ± 0.05Δ | <1.0Δ | <1.0Δ | <1.0Δ | <1.0Δ |
| BA | 6.08 ± 0.03 | 6.02 ± 0.04 | 6.46 ± 0.01 | 7.32 ± 0.08 | 8.67 ± 0.14 | 8.52 ± 0.03 |
| MP | 6.08 ± 0.03 | 6.04 ± 0.05 | 6.32 ± 0.03 | 6.63 ± 0.03 | 8.36 ± 0.05 | 8.45 ± 0.11 |
| OA/BA | 6.08 ± 0.03 | 4.74 ± 0.16Δ | 5.1 ± 0.32Δ | 4.54 ± 0.26Δ | 7.04 ± 0.02Δ | 7.69 ± 0.08Δ |
| OA/MP | 6.08 ± 0.03 | <1.0*Δ | <1.0*Δ | <1.0*Δ | <1.0*Δ | <1.0*Δ |
| OF/BA | 6.08 ± 0.03 | 4.49 ± 0.09Δ | 4.42 ± 0.08Δ | 5.53 ± 0.13Δ | 7.93 ± 0.06Δ | 7.25 ± 0.15*Δ |
| OF/MP | 6.08 ± 0.03 | <1.0*Δ | <1.0*Δ | <1.0*Δ | <1.0*Δ | <1.0*Δ |
| OB/BA | 6.08 ± 0.03 | 2.39 ± 0.18Δ | 1.60 ± 0.18Δ | 2.14 ± 0.11Δ | 4.57 ± 0.33Δ | 6.85 ± 0.09Δ |
| OB/MP | 6.08 ± 0.03 | <1.0Δ | <1.0Δ | <1.0Δ | <1.0Δ | <1.0Δ |
| OB' | 6.08 ± 0.03 | 6.03 ± 0.05 | 6.83 ± 0.04 | 8.16 ± 0.08 | 8.97 ± 0.07 | 8.70 ± 0.03 |
| OB'/BA | 6.08 ± 0.03 | 5.97 ± 0.03 | 6.42 ± 0.02 | 7.29 ± 0.04 | 8.79 ± 0.18 | 8.56 ± 0.02 |
| OB'/MP | 6.08 ± 0.03 | 6.06 ± 0.03 | 6.24 ± 0.05 | 6.39 ± 0.12 | 7.90 ± 0.22 | 8.46 ± 0.03 |

OA = oil of anise at 0.2%
OF = oil of fennel at 0.2%
OB = oil of basil at 0.2%
OB' + oil of basil at 0.02%
BA = benzoic acids at 0.1%
MP = methyl paraben at 0.1%
*= synergistic inhibition
Δ = p < 0.05 inhibition compared to that of corresponding control
The $\log_{10}$ of the mean of the count from three separate experiments as shown

TABLE 2

Inhibition of *Listeria monocytogenes* and *Salmonella enteriditis* by combinations of trans-anethole, estragole or fenchone with methyl paraben at 37° C. over a period of 48 hrs. The starting inoculum for *L. monocytogenes* was 6.4 ± 0.04 and for *S. enteriditis* it was 5.9 ± 0.01

| Time | 1 hr | 4 hrs | 8 hrs | 24 hrs | 48 hrs |
|---|---|---|---|---|---|
| 2A *Listeria monocytogenes* | | | | | |
| Control | 6.5 ± 0.02 | 7.2 ± 0.04 | 8.2 ± 0.02 | 9.3 ± 0.04 | 9.1 ± 0.04 |
| Estragole | 5.9 ± 0.05 | 5.6 ± 0.07Δ | 5.5 ± 0.06Δ | 4.9 ± 0.08Δ | 4.7 ± 0.09Δ |
| Trans-anethole | 6.1 ± 0.04 | 6.3 ± 0.1 | 6.7 ± 0.2 | 9.0 ± 0.1 | 9.0 ± 0.01 |
| Fenchone | 2.7 ± 0.2Δ | 1.9 ± 0.08Δ | <1.0Δ | <0.1Δ | <1.0Δ |
| Methyl paraben | 6.5 ± 0.01 | 6.9 ± 0.01 | 7.7 ± 0.01 | 9.3 ± 0.01 | 9.2 ± 0.01 |
| Estragole and methyl paraben | 5.3 ± 0.06 | 5.3 ± 0.05Δ | 3.7 ± 0.1Δ* | 2.3 ± 0.2Δ* | 1.7 ± 0.1Δ* |
| Trans-anethole & methyl paraben | 6.0 ± 0.03 | 6.0 ± 0.01Δ | 5.9 ± 0.01Δ* | 5.0 ± 0.1Δ* | 4.7 ± 0.3Δ* |
| Fenchone and methyl paraben | 3.3 ± 0.3Δ | 1.8 ± 0.2Δ | <1.0Δ | <1.0Δ | <1.0Δ |
| 2B *Salmonella enteriditis* | | | | | |

REFERENCES

[1] Office for National Statistics (1996) in Monitor Population and Health. MB2 96/6 (Sept.) St. Catherine's House, 10 Kingsway, London WG2B 6JP.

[2] Farber, J. M. and Peterkin, P. I. (1991) *Listeria monocytogenes*, a food-borne pathogen. Microbiological Reviews. 55 (3) 476–511.

[3] Gould, G. W. (1995) *New Methods of Food Preservation* Blackie Academic and Professional of Chapman and Hall Publishers. Glasgow G64 2NZ.

[4] Doores, S. (1993) organic Acids in *Antimicrobials in Food* (1993) ed. by P. M. Davidson and A. L. Branen. Marcel Dekker Publisher. N.Y. USA.

[5] Delves-Broughton (1990) Nisin and its uses as a food preservative. *Food Technology* 44 (11) 100–118.

[6] Walker, S. J. and Stringer, M. F. (1987) Growth of *Listeria monocytogenes* and *Aeromonas hydrophila* at chill temperatures. J. of Applied Bacteriology. 63. R20.

[7] Deans, S. G. and Ritchie, G. (1987) Antibacterial properties of plant essential oils. *International Journal of Food Microbiology*. 5,156–180.

[8] Tassov, C. C., Drosinos, E. H. and Nychas, G. J. E. (1995) Effects of essential oil from mint (*Mentha piperita*) on *Salmonella enteriditis* and *Listeria monocytogenes* in model food systems at 4° C. and 10° C. J. of Applied Bateriology. 78, 593–600.

[9] Chipley, J. R. (1993) Sodium Benzoate and Benzoic Acid in *Antimicrobials in Food* (1993) ed. by P. M. Davidson and A. L. Branen. Marcel Dekker Publisher. N.Y. USA.

[10] Lueck, E. (1980) *Antimicrobial Food Additives*. Springer-Verlag. N.Y. USA.

[11] Code of Federal Regulations (1991) *Title 21. Food and Drugs*. Parts 170–199. Office of Federal Regulations. National Archives Records Services, General Services Administration, Washington D.C. USA.

[12] Eliopoulos, G. M. and Moellering, R. C. (1991) *Antimicrobial Combinations in Antibiotics in Laboratory Medicine*. ed. V. Lorian. Williams and Williams Publisher. 34d Edition pg. 432.

[13] Mims, C. A. Playfair, J. H. L., Roitt, I. M., Wakelin, D. and Williams, R. (1993) *Medical Microbiology* Mosby Publishers, London, UK.

[14] Max, B. (1992) This and That: the essential pharmacology of herbs and spices TIPS. 13, 15–20.

[15] Davidson, P. M. (1993) Parabens and Phenolic Compounds in *Antimicrobials in Food* ed. by P. M. Davidson and A. L. Branen. Marcel Dekker Publisher. N.Y. USA.

[16] Freese, E. (1978) Mechanism of growth inhibition by lipophilic acids. In *Pharmacological Effects of Lipids* ed. by J. J. Kabara. American Oil Chemists Society. Champaign I. L. p 123.

[17] Denyer, S. P., Hugo, W. B., and Harding, V. D. (1985) *Synergy in preservative combinations*. International Journal of Pharmaceutics. 25, 245–253.

[18] Jones, C. E., Shama, G., Jones, D., Roberts, I. S. and Andrew, P. W. C. (1997) Physiological and biochemical studies on psychotolerance in *Listeria monocytogenes*. Journal of Applied Bacteriology. 83. 31–35.

[19] Tisserand, R and Balais, TA Essential Oil Safety: A Guide for Health Care Professionals. Churchill Livingstone.

[20] Opdyke, D. L. J. (1978). Monographs of fragance, raw materials. Food and cosmetics Toxicology. 16.

[21] Opdyke, D. L. J. (1973). Monographs of fragance raw materials. Food and Cosmetics Toxicology. 16.

[22] Zangouras. A et al. (1981). Dose-dependant conversion of estragole in the rat mouse to carcinogenic metabolite 1st Lydroxyestragole. Biochemical Pharmacology. 30. 1383–1386.

[23] Anthony. A. et al, (1987). Metabolism of estragole in rat and mouse and influence of dose size on excretion of the proximate carcinogen 1-Lydroxyestragole. Food and Chemical Toxicology 25. 799–806.

What is claimed is:

1. A formulation comprising:
a combination of at least one plant oil chosen from oils of fennel and, basil or one or more active ingredients thereof together with at least one of the group chosen from methyl paraben, ethyl paraben, propyl paraben and butyl paraben,
wherein said one or more active ingredients are trans-anethole, fenchone or estragole, wherein the concentration of fennel oil or basil oil or active ingredient thereof is between 0.01% to 1%, and wherein said formulation is used as a micro-organism inhibitor.

2. The formulation as claimed in claim 1 wherein the concentration of methyl paraben, ethyl paraben, propyl paraben or butyl paraben is from 0.01% to 1%.

3. The formulation according to claim 2 wherein the formulation is in combination with a pharmaceutically acceptable carrier.

4. A medicament to inhibit micro-organism growth comprising a formulation as claimed in claim 2.

5. The formulation as claimed in claim 2 in a spray formulation.

6. The formulation according to claim 1 wherein the formulation is in combination with a pharmaceutically acceptable carrier.

7. A medicament to inhibit micro-organism growth comprising a formulation as claimed in claim 1.

8. The formulation as claimed in claim 1 in a spray formulation.

9. The formulation according to claim 1, wherein said combination comprises oil of fennel at a concentration in the range of 0.1 to 0.4%.

10. The formulation according to claim 9, wherein said combination comprises methyl paraben at a concentration in the range of 0.05 to 0.5%.

11. A medicament to inhibit micro-organism growth comprising a formulation as claimed in claim 10.

12. A medicament to inhibit micro-organism growth comprising a formulation as claimed in claim 9.

13. The formulation according to claim 1, wherein said combination comprises oil of basil at a concentration in the range of 0.01 to 0.5%.

14. The formulation according to claim 13, wherein said combination comprises oil of basil at a concentration in the range of 0.05 to 0.5%.

15. A medicament to inhibit micro-organism growth comprising a formulation as claimed in claim 14.

16. A medicament to inhibit micro-organism growth comprising a formulation as claimed in claim 13.

* * * * *